United States Patent [19]

Pruckmayr

[11] 4,230,892

[45] Oct. 28, 1980

[54] ALCOHOLYSIS PROCESS FOR PREPARING POLY-(TETRAMETHYLENE ETHER) GLYCOL

[75] Inventor: Gerfried Pruckmayr, Media, Pa.

[73] Assignee: E. I. Du Pont de Nemours and Company, Wilmington, Del.

[21] Appl. No.: 59,137

[22] Filed: Jul. 20, 1979

Related U.S. Application Data

[63] Continuation-in-part of Ser. No. 905,972, May 15, 1978, abandoned, and a continuation-in-part of Ser. No. 767,510, Feb. 14, 1977, abandoned, and a continuation-in-part of Ser. No. 672,557, Mar. 31, 1976, abandoned.

[51] Int. Cl.$^3$ .............................................. C07C 43/11
[52] U.S. Cl. ................................................... 568/617
[58] Field of Search ......................................... 568/617

[56] References Cited

U.S. PATENT DOCUMENTS

| | | | |
|---|---|---|---|
| 2,476,052 | 7/1949 | Lippincott | 560/234 |
| 2,476,053 | 7/1949 | Lippincott | 560/234 |
| 3,776,948 | 12/1973 | Kleeman et al. | 60/240 |
| 3,864,287 | 2/1975 | Matsuda | 260/24 |
| 3,981,931 | 9/1976 | Smith | 560/243 |

OTHER PUBLICATIONS

Hill et al., JACS, 45, 1923, 3130.
Finch, Polyvinyl Alcohol, John Wiley & Sons, New York, 1973, p. 94.

*Primary Examiner*—Howard T. Mars

[57] ABSTRACT

Poly(tetramethylene ether) ester is converted to poly(tetramethylene ether) glycol by alcoholysis using as a catalyst an oxide, hydroxide or alkoxide of calcium, strontium, barium or magnesium.

7 Claims, 1 Drawing Figure

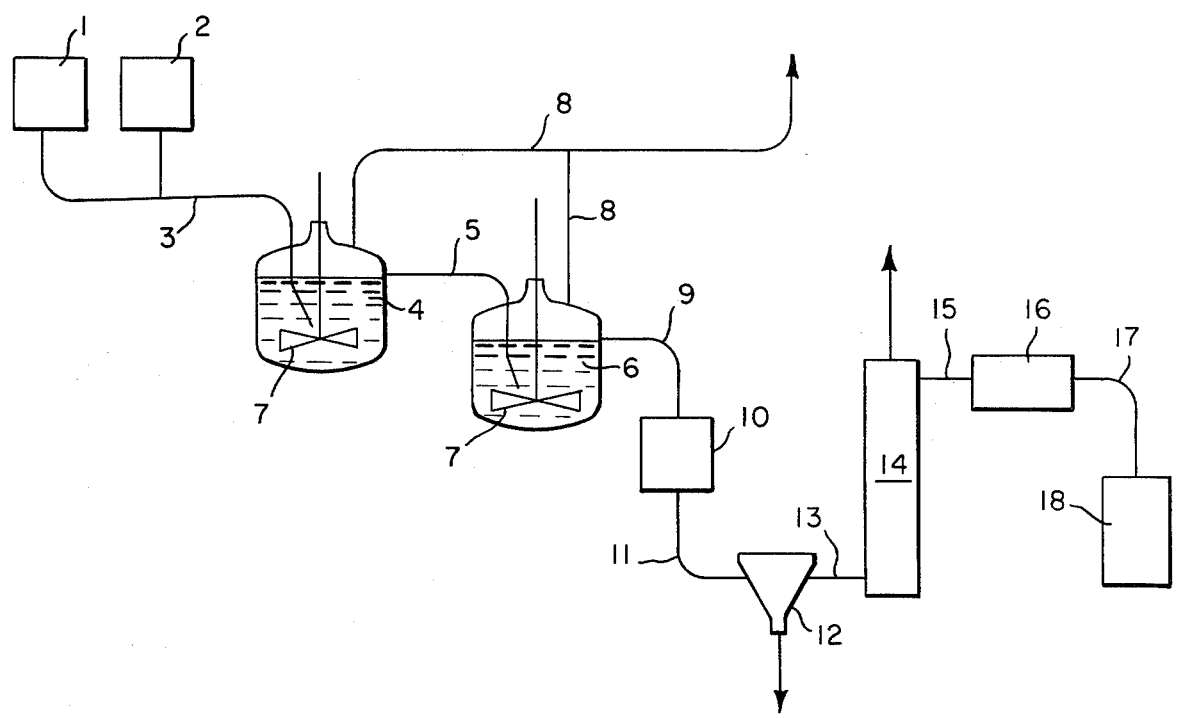

ALCOHOLYSIS PROCESS FOR PREPARING POLY-(TETRAMETHYLENE ETHER) GLYCOL

CROSS-REFERENCE TO RELATED APPLICATIONS

This application is a continuation-in-part of application Ser. No. 905,972, filed May 15, 1978, as a continuation-in-part of application Ser. No. 767,510, filed Feb. 14, 1977, as a continuation-in-part of application Ser. No. 672,557, filed Mar. 31, 1976 all abandoned.

BACKGROUND AND SUMMARY OF THE INVENTION

Poly(tetramethylene ether) glycol (PTMEG), is a commodity in the chemical industry, widely used in the preparation of polyesters and polyurethanes. A variety of methods is known for manufacturing PTMEG, one being that disclosed in Belgian Pat. No. 853,028.

In that method, tetrahydrofuran is polymerized in the presence of acetic anhydride to form poly(tetramethylene ether) diacetate (PTMEA). This diacetate must then be converted to PTMEG. Conventional processes can be used for this conversion, but these leave soluble catalyst residues which contaminate the final product and may make it unfit for certain uses.

It has now been found, according to this invention, that the conversion can be easily accomplished to give nearly catalyst-free PTMEG if it is done by alcoholysis using an alkanol of 1–4 carbon atoms, and using as a catalyst an oxide, hydroxide or alkoxide of calcium, barium, strontium or magnesium.

DESCRIPTION OF THE DRAWING

The drawing is a schematic diagram of a multi-stage apparatus which can be used in performing the process of the invention.

DETAILED DESCRIPTION OF THE INVENTION

The process of the invention proceeds according to the following illustrative equation:

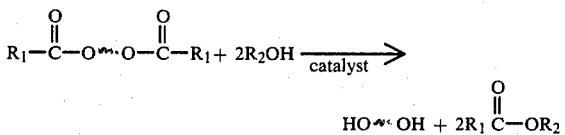

where
$R_1$ and $R_2$ are alkyl radicals of 1–4 carbon atoms, and
⚊ is a poly(tetramethylene ether) polymer chain.

To practice the invention, a mixture of a poly(tetramethylene ether) diester starting material, catalyst and alkanol is first prepared. This can be done by simply mixing the components together in a reactor, in any order. Preferably, the catalyst is first slurried in the alkanol and this slurry is then mixed with a solution of the diester in alkanol.

The mixture is prepared so that it contains about 5–80%, preferably 20–60% (by the total weight of diester and alkanol) of diester, and 20–95%, preferably 40–80% (by weight of the total of diester and alkanol) of alkanol. The catalyst is present in the mixture at a concentration of 1–25 mol percent based on the diester, preferably 8–20 mol percent, i.e., substantially less than stoichiometric quantities.

The diester starting material in this mixture will, in the usual case, be a PTMEA produced by the process shown in Belgian Pat. No. 853,028, although other such esters, such as for example the propionates and butyrates, can also be used.

The catalyst used in this mixture is an oxide, hydroxide or alkoxide (in which the alkyl group contains 1–4 carbon atoms) of calcium, barium, strontium or magnesium. The preferred catalyst is calcium oxide. The catalyst is ordinarily particulate and is preferably in powder form.

The alkanol in the mixture is one containing 1–4 carbon atoms. Methanol is preferred, especially when calcium oxide is used as the catalyst.

It is important that the polymeric diester starting material be neutral or nearly neutral, i.e., that it have a pH value of about 7 before the catalyst is added, for if the pH value is below about 7, the catalyst or parts thereof is converted to a catalytically inactive salt. The pH of the starting material can be brought to about 7 by conventional means, such as vacuum distillation.

The mixture is then brought to its boiling point and held there, with stirring, while vapors of the alkanol/alkyl ester azeotrope which form are continuously withdrawn from the reaction zone. In the usual case, the boiling point of the mixture will be in the range of about 50°–150° C. If temperatures higher than this are required, the reaction can be run under a pressure of up to 100 atmospheres. This boiling and withdrawal of azeotrope is continued until the alcoholysis is substantially complete, i.e., until no more alkyl acetate is detected in the azeotrope being removed, as determined by gas chromatography.

The process can be conducted batchwise or in continuous fashion. The continuous mode is preferred for its efficiency.

Although the process can be run in a single stage, it is preferably run in two or more stages, especially when run continuously, because this gives a higher degree of conversion. The continuous multi-stage process is run exactly as the one-stage process except that the contents of the first reactor are transferred sequentially to the others, where alcoholysis is completed. Residence time in each reactor is about 60–160 minutes.

It may be desirable that alkanol be continuously added to the secondary reactors in an amount equal to the amount of alkanol in the azeotrope withdrawn.

After the alcoholysis is complete, the catalyst and such other insoluble materials as may be present are removed from the reaction mass by conventional techniques such as filtration, decantation or centrifugation. Ordinarily and preferably, the catalyst is filtered from the reaction mass and recycled to one of the reactors, but the reaction mass can also be withdrawn from the reactor through a filter which holds back the catalyst and other insolubles and keeps them in the reactor.

It may also be desirable, before or after the separation of catalyst, to strip the reaction mass of residual alkanol and alkyl ester byproduct. This can be done by conventional engineering techniques.

The foregoing description will be more easily understood by referring to the drawing. In the apparatus shown, the catalyst is slurried in alkanol in tank 1 and the slurry is then fed into line 3 where it mixes with ester starting material from tank 2. The resulting mixture enters first reactor 4 near the vortex formed by the swirling reaction mass. Partially converted diester is withdrawn from reactor 4 through overflow line 5, which feeds the diester into second reactor 6, again into the vortex of the reaction mass. The masses in both reactors are stirred by paddles 7 and are kept at their boiling points by suitable means while vapors of alkanol/alkyl acetate azeotrope are withdrawn from the reactors through line 8 and then reprocessed as desired. Glycol product containing catalyst, residual alkanol and residual alkyl acetate overflows from reactor 6 through line 8 into holding tank 10. From there it is fed through line 11 to centrifuge 12 where the catalyst is removed. The glycol product is then fed through line 13 to column 14, where alkanol and alkyl ester are removed. Dry PTMEG is withdrawn from column 14 through line 15 and fed to filter 16 for final filtration. From there it flows through line 17 to storage tank 18.

The PTMEG product of the process can be put to any conventional use, such as the preparation of polyesters or polyurethanes, according to methods well known in the art.

EXAMPLES

Example 1

PTMEG was produced in an apparatus similar to that illustrated in the drawing. Both reactors were of 500 ml capacity and were arranged so that flow in lines 5 and 9 was by gravity.

A 40% by weight solution of PTMEA (number average molecular weight of 1070) in methanol was prepared in tank 1, and a 5% by weight slurry of calcium oxide in methanol was prepared in tank 2. The PTMEA solution was fed into first reactor 4 through line 3, at the rate of 4-5 ml per minute. The CaO slurry was fed into reactor 4 through line 3 at a rate which gave a reaction mixture containing 0.5%, by weight of the PTMEA, (10 mol percent based on the PTMEA) of CaO. From reactor 4, the reaction mixture was allowed to flow through line 5 into second reactor 6.

The temperature of the reaction mass in each reaction was kept at about 68° C. and the vapors of the methanol/methyl acetate azeotrope which formed in each reactor were continuously withdrawn through line 8. Residence time in each reactor was about 90 minutes.

From the second reactor, the reaction mass was allowed to flow to a filter, where the calcium oxide and other insoluble materials were removed, and thence to a rotary evaporator, where residual methanol and methyl acetate were removed and the product dried to constant weight.

Four hundred thirty grams of PTMEG (number average molecular weight of 980) were recovered after 8 hours of continuous operation. Infrared spectroscopic analysis of the product showed an absence of carbonyl absorption at 1750 cm$^{-1}$, indicating substantially complete conversion of the PTMEA to PTMEG.

Example 2

A 25 g sample of PTMEA (number average molecular weight of 1070) was dissolved in 100 ml of methanol. After addition of 0.5 g (9 mol percent based on PTMEA) of calcium hydroxide, the mixture was heated to 65° C. and held there for 3 hours, with stirring, while vapors of the methanol/methyl acetate azeotrope which formed were withdrawn.

The product was then dried for 1 hour at 85° C. in a vacuum of about 1 mm of mercury. Filter aid, 0.1 g, was added and the product was filtered to remove insoluble material.

The resulting PTMEG product (number average molecular weight of 980) contained less than 2 ppm of calcium, as determined by atomic absorption. Infrared spectroscopic analysis demonstrated that the conversion to PTMEG was substantially complete.

Example 3

A 25 g sample of PTMEA (number average molecular weight of 1070) was dissolved in 100 ml of methanol, as in Example 2. Instead of calcium hydroxide, 0.5 g (10 mol percent based on PTMEA) of calcium oxide was added, and the mixture processed as in Example 2.

Infrared spectroscopic analysis of the PTMEG product (number average molecular weight 980) showed that conversion to PTMEG was substantially complete.

Example 4

A 36 g sample of PTMEA (number average molecular weight of 1280) was dissolved in 160 ml of methanol, and 1 g (18.7 mol percent based on PTMEA) of barium oxide was added to the solution. The resulting slurry was heated to 65° C. and held there for 3 hours, while vapors of the methanol/methyl acetate azeotrope which formed were continuously withdrawn.

The resulting product was dried and processed as in Example 2, to give PTMEG (number average molecular weight 1200).

I claim:

1. A process for converting a poly(tetramethylene ether) diester to PTMEG, the process comprising
   (A) preparing a mixture of
      (1) a poly(tetramethylene ether) diester having a pH of about 7,
      (2) an alkanol of 1-4 carbon atoms, and
      (3) 1-25 mol percent, based on the diester, of a catalyst which is an oxide or hydroxide of calcium, strontium or barium;
   (B) bringing the mixture to its boiling point and holding it there while the vapors of the alkanol/alkyl ester azeotrope which form are continuously removed from the reaction zone, until conversion is substantially complete; and then
   (C) removing the catalyst, and optionally the residual alkanol and residual alkyl ester, from the reaction mass.

2. The process of claim 1 wherein step (B) is performed in stages.

3. The process of claim 1 run in continuous fashion.

4. The process of claim 1 wherein the catalyst in (A) (3) is calcium oxide.

5. The process of claim 1 wherein the mixture of (A) contains 10-20 mol percent, based on the diester of catalyst.

6. A process for converting PTMEA to PTMEG, the process comprising
   (A) preparing a mixture of
      (1) 20-60%, by the total weight of PTMEA and methanol, of PTMEA having a pH of about 7,
      (2) 40-80%, by the total weight of PTMEA and methanol, of methanol, and
      (3) 8-20 mol percent, based on the PTMEA, of calcium oxide;
   (B) bringing the mixture to its boiling point and holding it there while the vapors of the methanol/methyl acetate azeotrope which form are continuously removed from the reaction zone, until conversion is substantially complete; and then
   (C) removing the calcium oxide, residual methanol and residual methyl acetate from the reaction mass.

7. The process of claim 6 run in continuous fashion.

* * * * *